United States Patent [19]
Hodosh

[11] Patent Number: 6,159,161
[45] Date of Patent: *Dec. 12, 2000

[54] MICROPROCESSOR-CONTROLLED FLUID DISPENSING APPARATUS

[76] Inventor: Milton Hodosh, 2 Harian Dr., Providence, R.I. 02906

[ * ] Notice: This patent is subject to a terminal disclaimer.

[21] Appl. No.: 09/111,953

[22] Filed: Jul. 8, 1998

Related U.S. Application Data

[63] Continuation-in-part of application No. 08/546,382, Oct. 20, 1995, Pat. No. 5,807,334.

[51] Int. Cl.⁷ ........................................................ A61B 5/00
[52] U.S. Cl. ............................ 600/561; 604/118; 604/131
[58] Field of Search .................................... 604/131, 155, 604/151, 152, 154; 600/561

[56] References Cited

U.S. PATENT DOCUMENTS

| | | |
|---|---|---|
| 2,574,263 | 11/1951 | Hinds . |
| 3,395,704 | 8/1968 | Frey et al. . |
| 3,768,472 | 10/1973 | Hodosh et al. . |
| 3,811,442 | 5/1974 | Maroth . |
| 4,273,122 | 6/1981 | Whitney et al. . |
| 4,560,979 | 12/1985 | Rosskopf . |
| 4,627,835 | 12/1986 | Fenton, Jr. . |
| 4,668,220 | 5/1987 | Hawrylenko . |
| 4,676,122 | 6/1987 | Szabo et al. . |
| 4,787,893 | 11/1988 | Villette . |
| 4,897,080 | 1/1990 | Hamidi . |
| 4,940,458 | 7/1990 | Cohn ........................................ 604/512 |
| 5,034,003 | 7/1991 | Denance . |
| 5,176,646 | 1/1993 | Kuroda . |
| 5,180,371 | 1/1993 | Spinello ................................. 604/118 |
| 5,232,449 | 8/1993 | Stern et al. . |
| 5,322,511 | 6/1994 | Armbruster et al. . |
| 5,599,301 | 2/1997 | Jacobs et al. .............................. 604/65 |
| 5,750,029 | 5/1998 | Houck et al. ........................... 210/634 |
| 5,807,334 | 9/1998 | Hodosh et al. .......................... 604/131 |

Primary Examiner—Cary O'Connor
Assistant Examiner—Pamela Wingood
Attorney, Agent, or Firm—Salter & Michaelson

[57] ABSTRACT

A fluid dispenser includes a hollow housing having an elongate chamber formed therein. A power supply is located within the chamber of the housing, the power supply being in electrical communication with a variable speed motor also located within the chamber of the housing. A switch, accessible from outside the housing, is in electrical communication with the power supply and motor for selectively operating the motor from a non-operable condition to an operable condition. A microprocessor controls the speed of the motor, enabling the fluid dispenser to deliver fluid at a wide range of speeds.

17 Claims, 9 Drawing Sheets

MICROPROCESSOR-CONTROLLED FLUID DISPENSING APPARATUS

CROSS-REFERENCE TO RELATED APPLICATIONS

This application is a continuation-in-part of application Ser. No. 08/546,382, filed Oct. 20, 1995, now U.S. Pat. No. 5,807,334, issued Sep. 15, 1998.

BACKGROUND OF THE INVENTION

1. Field of the Invention

This invention relates generally to fluid dispensers, and more particularly to a microprocessor-controlled fluid dispensing apparatus capable of dispensing anesthetic (e.g., lidocaine and novocaine) at a controlled, steady rate which is free of surge.

2. Discussion of the Related Art

During certain surgical and dental procedures, and particularly the latter, it is common practice to administer an anesthetic, such as lidocaine, in order to temporarily anesthetize sensory nerves so that the patient will not be compelled to endure pain. However, the administration of the anesthetic is, to most patients, extremely unpleasant and often painful. It is relatively well-known that the primary cause of pain and discomfort attendant to the administration of a liquid anesthetic, such as lidocaine, is the fact that the conventional injection apparatus administers the anesthetic too quickly and without sufficient uniformity. It is further relatively well-known that if the anesthetic is administered slowly and uniformly, almost on a drop-by-drop basis, remarkably little or no pain or discomfort results.

Regardless of the specific nature of the injection, the fact of the matter is that there are numerous types of injections in which it is highly desirable to control the injection speed so that the anesthetic is injected at a controlled rate that does not illicit a painful response in the patient. Where such requirements exist, hand syringes depend upon the manual dexterity of the person administering the same and have proven unsatisfactory.

SUMMARY OF THE INVENTION

Thus, there is presently a need for a fluid dispensing apparatus which can deliver anesthetic in a consistent, uniform, and nearly painless manner.

As fluid is injected into a tissue site, the the tissue expands to absorb the fluid. As the tissue expands, the pressure within the tissue increases. When the pressure within a particular tissue site increases above a normal pressure which is tolerable by the tissue, the brain is signaled to induce a painful response. Accordingly, the injection of fluids into tissue should be done at a rate that does not increase the pressure of the tissue above the tissue's normal pressure, which causes pain. While injecting fluid on a drop-by-drop basis can alleviate the problems associated with injections, such a technique is very time consuming and uncomfortable for the patient.

Accordingly, among the several objects of the present invention are the provision of an improved fluid dispensing apparatus which is capable of automatically dispensing fluid from a carpule in a controlled and uniform manner; the provision of such an apparatus which is capable of aspirating; the provision of such an apparatus which is battery operated thereby freeing the apparatus from external cords and the like; the provision of such an apparatus which incorporates a rechargeable battery; the provision of such an apparatus having a pen light feature for illuminating the space inside the patient's mouth; the provision of such an apparatus which is light and compact; the provision of such an apparatus which is simple in design and cost-efficient to manufacture; and the provision of such an apparatus which is durable in use.

In general, a fluid dispenser of the present invention for dispensing fluid from a carpule having an axially slidable piston comprises a hollow housing having an elongate chamber formed therein. The housing extends generally along an axis, and is constructed and arranged to be gripped comfortably within a person's hand. A carpule receiving member, which is attached to the housing at one end thereof, has means for receiving a needle at its other opposite end. The receiving member is adapted to receive a carpule having fluid therein which is ejected through the needle. It is detachable for sterilization or replacement by a sterile disposable component. A power supply is located within the chamber of the housing, the power supply being in electrical communication with a motor also located within the chamber of the housing and having a drive mechanism which is rotatably driven. A switch, accessible from outside the housing, is in electrical communication with the power supply and motor for selectively operating the motor from a non-operable condition in which the power supply is electrically disconnected from the motor to an operable condition in which the power supply is electrically connected to the motor and supplies power thereto. A microprocessor controls an operating speed of the motor. A rack member, disposed within the chamber of the housing along the axis, comprises an elongate body having an end portion engagable with the piston of the carpule and teeth formed on a side thereof which are engagable with the drive mechanism for moving the rack member linearly from a position in which the end portion is spaced from the carpule piston to a position in which the end portion engages the carpule piston so as to effect the dispensing of fluid from the carpule and through the needle at a controlled rate. The microprocessor, by controlling the operating speed of the motor, controls the pressure at which the fluid is dispensed from the carpule.

Other objects, features and advantages of the invention shall become apparent as the description thereof proceeds when considered in connection with the accompanying illustrative drawings.

BRIEF DESCRIPTION OF THE DRAWINGS

In the drawings, which illustrate the best mode presently contemplated for carrying out the present invention.

Corresponding reference numerals designate corresponding parts throughout the several views of the drawings.

DETAILED DESCRIPTION OF THE PREFERRED EMBODIMENT

Figure 1:
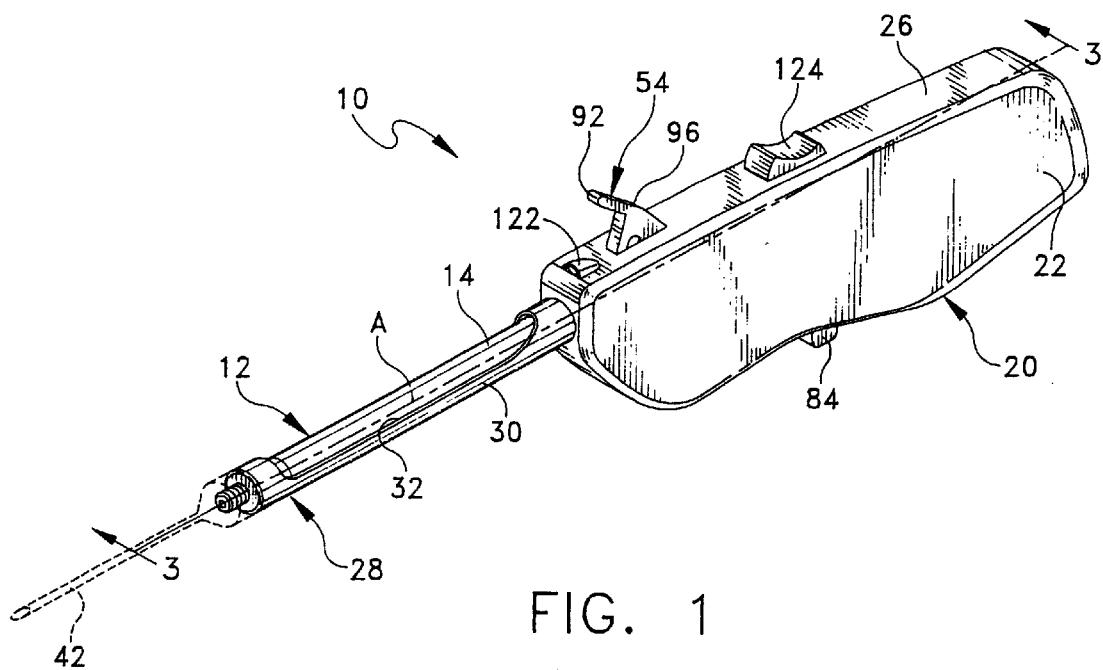
FIG. 1 is a perspective view of a fluid dispensing apparatus of the present invention.
Figure 2:
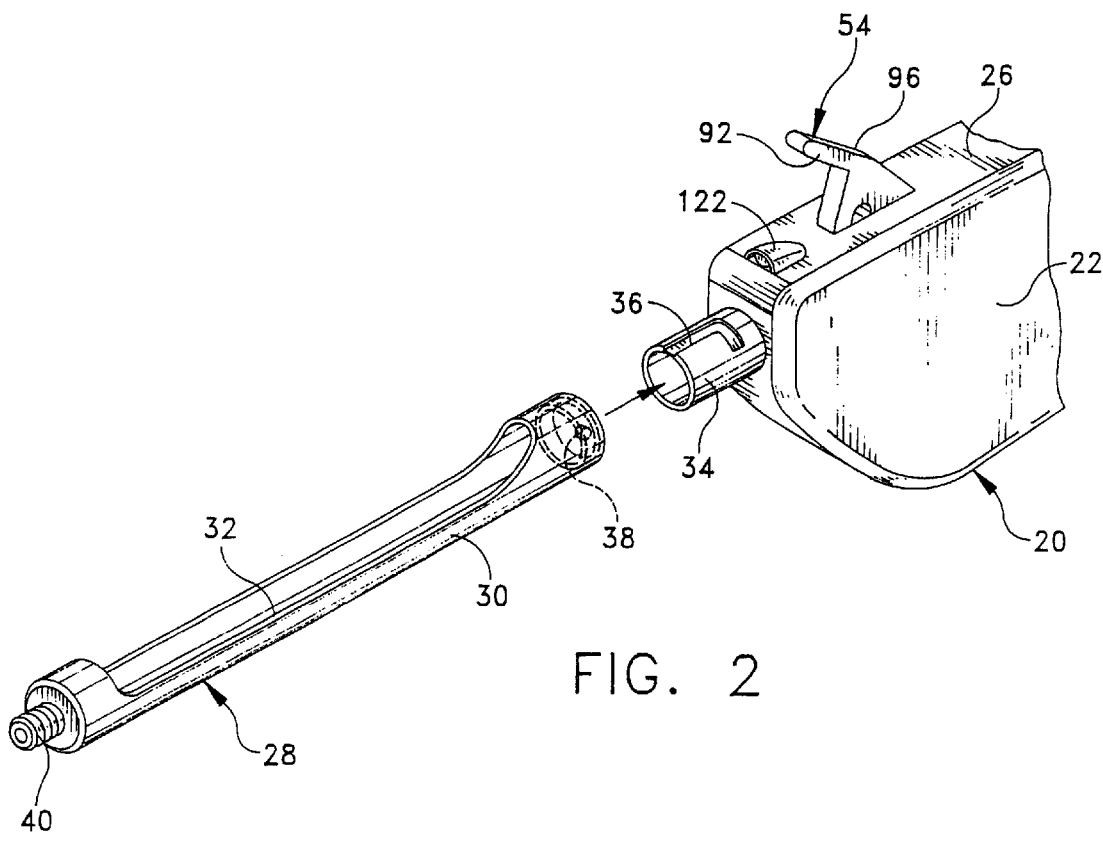
FIG. 2 is an enlarged perspective view of a portion of the apparatus illustrating the mounting of a carpule receiving member onto a housing of the apparatus.
Figure 3:
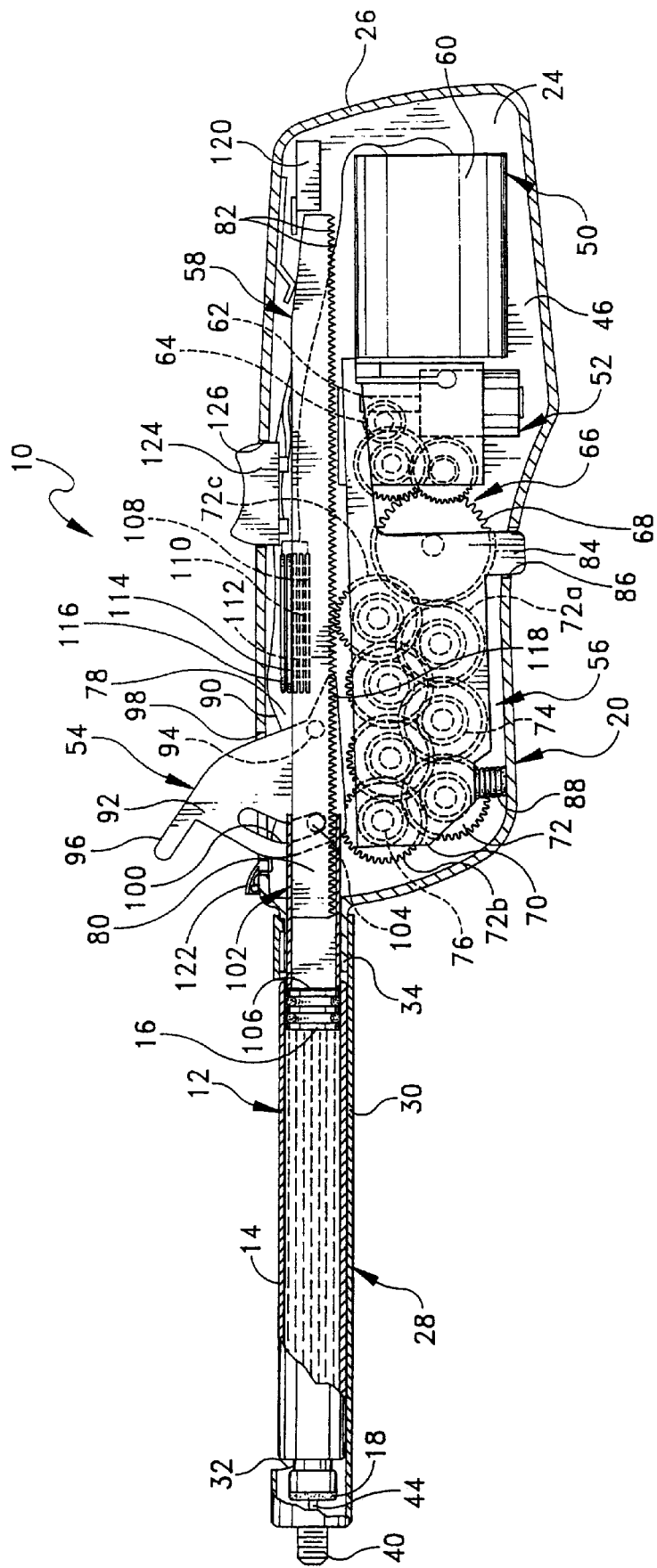
FIG. 3 is a cross-sectional view taken along line 3—3 of FIG. 1.

Referring now to the drawings, and more particularly to FIGS. 1 through 3, there is generally indicated at 10 a fluid dispensing apparatus of the present invention which is designed to dispense fluid from a carpule, generally indicated at 12. The carpule 12 is of the type having a cylindrical body 14 which is made from any suitable translucent material, such as clear plastic or glass, and an axially slidable piston 16 provided at an open end of the body 14. At the other end of the body 14, a rubber gasket 18 closes the open end. In the present invention, the carpule 12 preferably contains a suitable anesthetic for use during dental work. The manner in which the fluid is dispensed from the carpule 12 will be described in greater detail as the description of the apparatus 10 proceeds.

As shown, the apparatus 10 comprises an elongate housing generally indicated at 20 which extends along an axis A and has two relatively planar side walls 22, 24 and an outer peripheral wall 26 which interconnects the two side walls 22, 24. The arrangement is such that any one of the side walls 22, 24 is integrally formed with the outer peripheral wall 26 and the other of the side walls is attached to the other side wall 26 by means of screw fasteners (not shown). This construction is well-known in the art although the actual shape of the housing is not disclosed in any of the aforementioned prior art. Preferably, the housing 20 is fabricated from rigid material, such as plastic. As illustrated throughout the drawings, the housing 20 of the fluid dispensing apparatus 10 differs significantly from other prior art devices, such as the gun-shaped dispenser disclosed in U.S. Pat. No. 3,768,472, in that it is relatively compact and can be held in the operator's hand much like a pen. This results in the operator being able to hold the apparatus 10 with greater ease and dexterity.

The forward end of the housing 20 is constructed to receive a carpule receiving member, generally indicated at 28, which can be fabricated from autoclavable plastic or from reusable stainless steel. Preferably, the receiving member 28 is removably mounted on the housing 20 so that it can be removed for cleaning and sterilization, or to be replaced by a sterilized disposable member 28. As most clearly illustrated in FIG. 2, the carpule receiving member 28 comprises an outer cylindrical wall 30 that has an elongate slot 32 formed therein which is sized for receiving the carpule 12. This also enables the person administering the anesthetic to view the carpule 12 which is received within the slot 32 of the receiving member 28. The carpule receiving member 28 is releasably mounted on the housing 20 by a bayonet type of mount or the like. Carpule receiving member 28 may be reusable and sterilized between each use, or it may be presterilized and disposable.

More specifically, the housing 20 of the apparatus 10 includes a sleeve 34 which is mounted axially along axis A, the sleeve 34 including an L-shaped slot 36 formed therein. The wall 30 of the receiving member 28 is sized to receive the sleeve 34 therein when mounting the receiving member 28 to the housing 20. A detent member 38 is formed on the inner surface of the wall 30, the detent member 38 being received in the L-shaped slot 36 when mounting the receiving member 28 thereto. The receiving member 28 is secured to the housing 20 by axially sliding it over the sleeve 34 with the detent member 38 in the long leg of the L-shaped slot 36 until the sleeve 34 is nearly completely disposed within the cylindrical wall 30. At this point, the receiving member 28 is rotated clockwise for firmly securing the receiving member 28 to the housing 20, the detent member 38 being held secure by the sleeve 34 within the short leg of the L-shaped slot 36.

Figure 4:
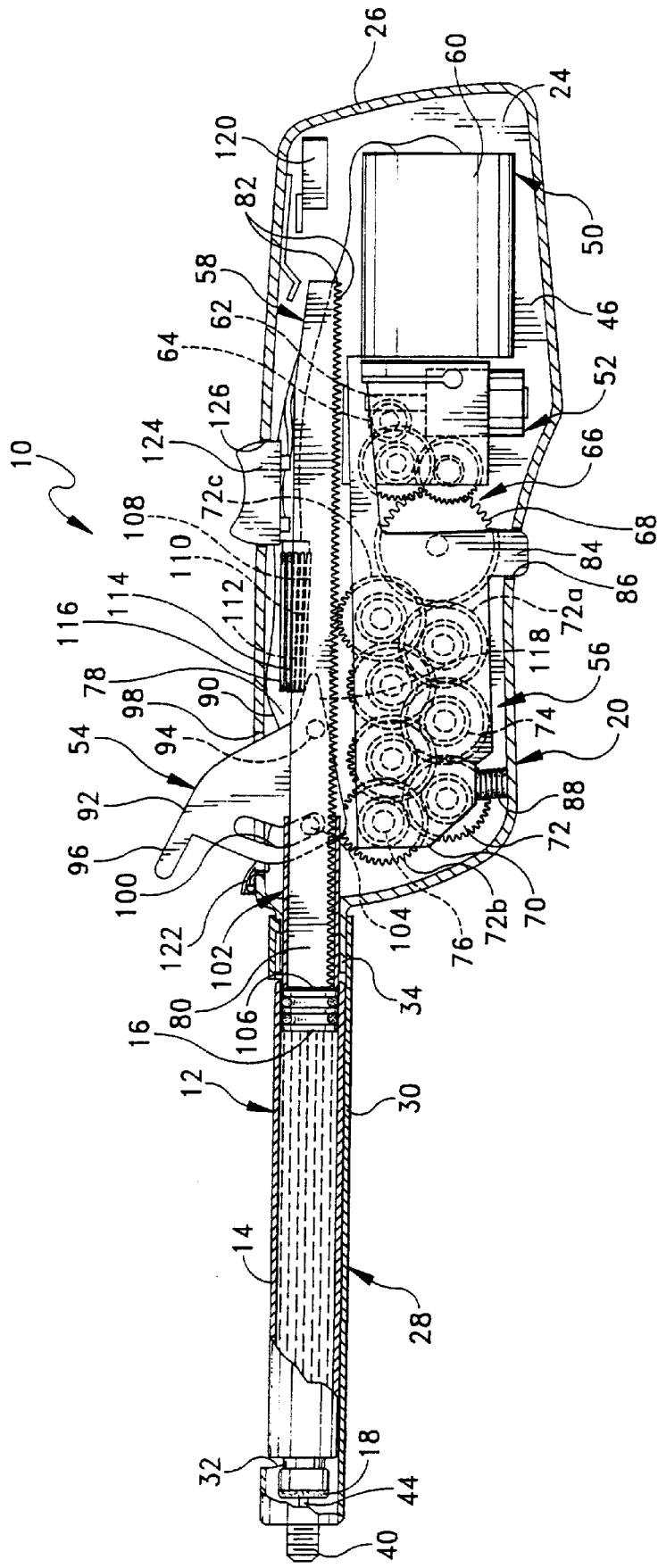
FIG. 4 is a cross-sectional view similar to FIG. 3 illustrating the apparatus in an aspirating mode.
Figure 5:
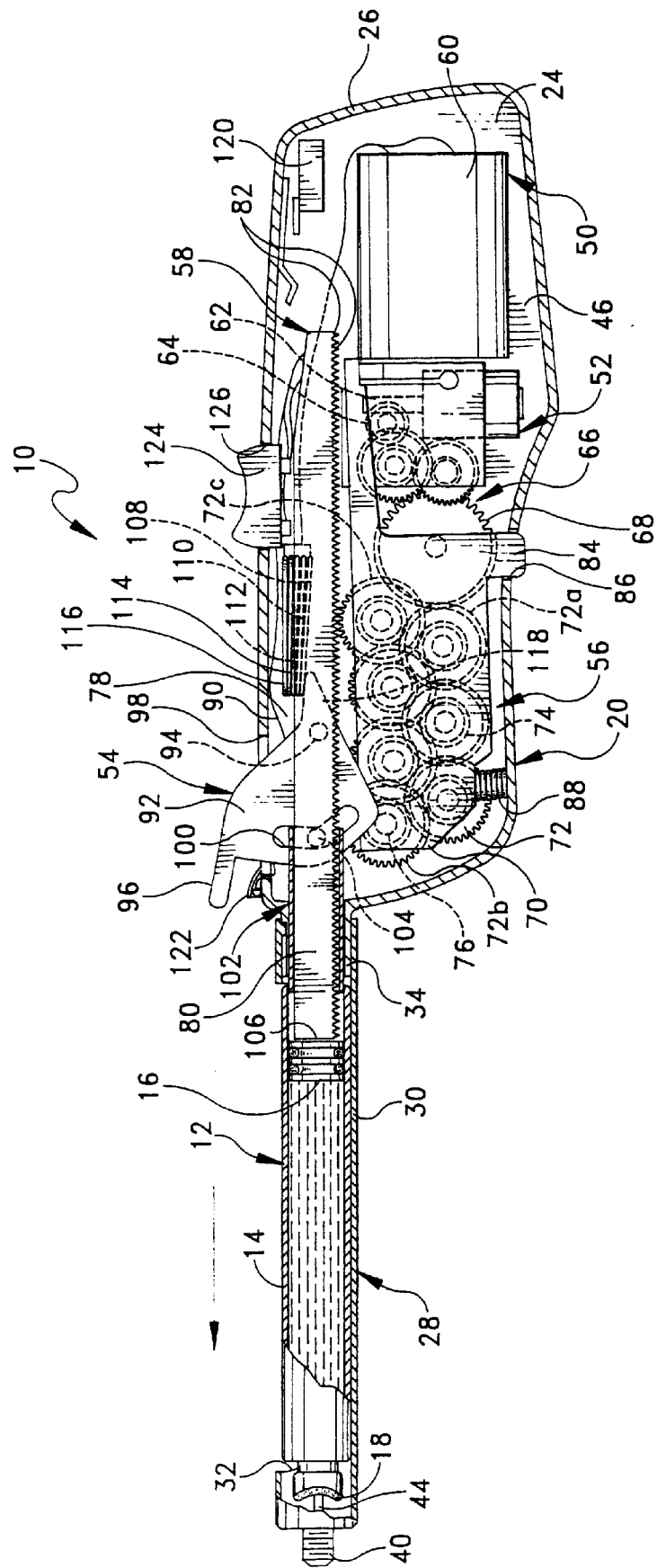
FIG. 5 is a cross-sectional view similar to FIGS. 3 and 4 illustrating the apparatus in fast forward operating mode.
Figure 6:
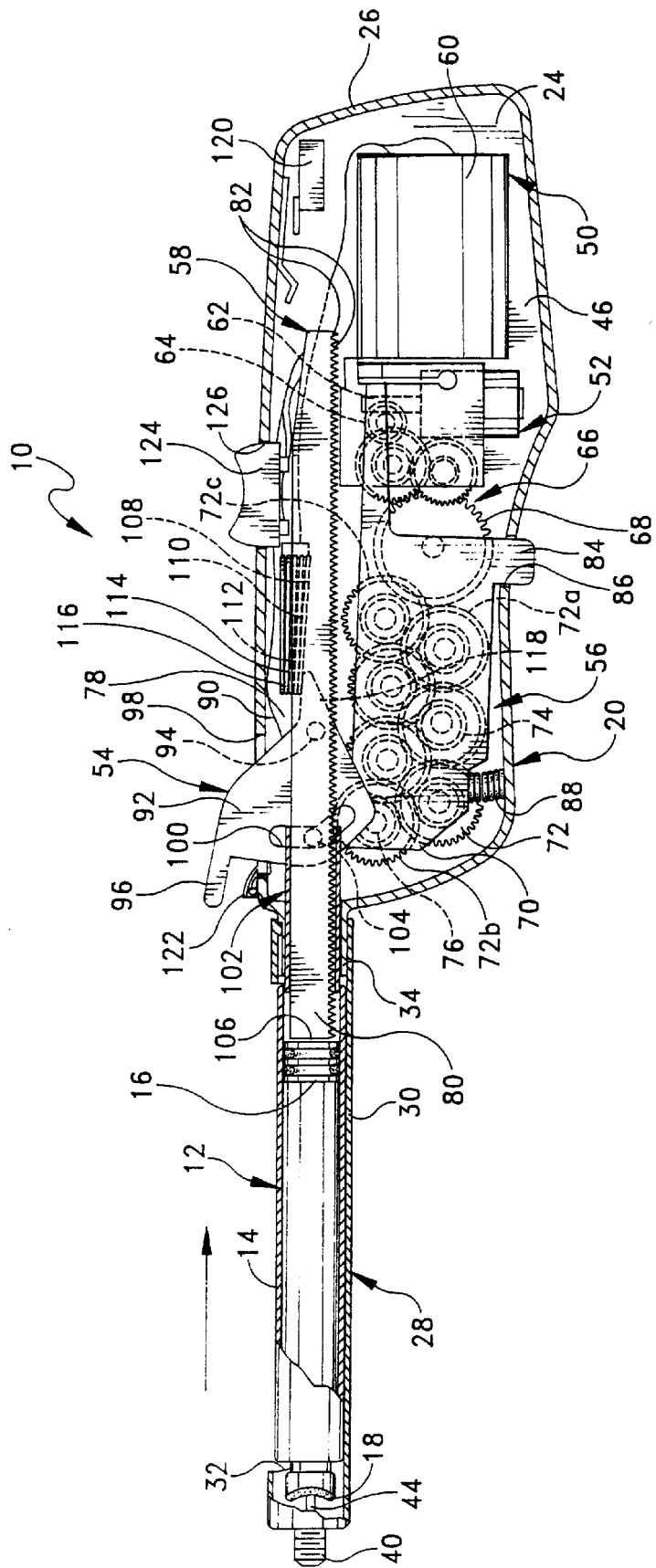
FIG. 6 is a cross-sectional view similar to FIGS. 3 through 5 illustrating the apparatus in slow forward operating mode.

The forward end of the carpule receiving member 28 has a cylindrical threaded portion 40 with outer male threads formed therein for releasably securing a needle 42 thereto (see FIG. 1). As shown, the needle has an elongate cylindrical member and in internal needle portion (not shown) which punctures the rubber gasket 18 of the carpule in the well-known manner. The purpose of this construction is for enabling the operator of the apparatus 10 to remove the needle 42 and replace it after each use. Integrally formed with the threaded portion 40 is an annular stem portion 44 which deflects the rubber gasket 18 of the carpule 12 when the carpule 12 is disposed within the receiving member 28. The stem portion 44 is designed to receive therein the internal needle portion of the needle. FIGS. 4 through 6 illustrate the stem portion 44 deflecting the rubber gasket 18 of the carpule 12.

Turning now to FIGS. 3 through 7, the housing 20 of the apparatus 10 is of hollow construction having an elongate chamber 46 formed therein which contains the component parts for applying an axial force on the piston 16 of the carpule 12 for dispensing fluid at a slow and uniform rate therefrom. More specifically, the apparatus 10 includes, within the chamber 46 of the housing 20, a power supply, generally indicated at 50, a motor, generally indicated at 52, which is energized by the power supply 50, a switch, generally indicated at 54, for turning on and off the motor 52, a gear train, generally indicated at 56, for moving a rack member, generally indicated at 58, axially along axis A to compress the piston 16 of the carpule 12. Preferably, the power supply 50 includes a rechargeable battery 60; however, the apparatus 10 can include a power cord (not shown) for electrically connecting the apparatus 10 to an electrical wall outlet. The provision of a rechargeable battery 60 enables the operator of the apparatus 10 to freely move and operate it without the restrictions of an attached cord.

Preferably, the motor 52 is a single speed motor operable by means described below to achieve one of three speeds. The motor 52 has a core body and a drive shaft 62 which is rotatably driven by the motor 52 at one of three speeds. The drive shaft 62 has a worm gear 64 mounted thereon which engages and drives a group of six gears, generally designated 66, rotatably mounted on three shafts within the chamber 46. The arrangement is such that one large diameter gear and one small diameter gear are mounted on a shaft. The shafts of the spur gears are suitably mounted within the chamber 46 of the housing 20. The largest of the group of gears 66, gear 68, drives the gear train 56. The positioning and arrangement of the group of spur gears 66 need not be described in great detail since a person skilled in the art could use any number of gears and position them at any number of locations within the chamber 46 of the housing 20 for driving the gear train 56.

The gear train 56 includes a frame 70 which supports seven larger gears, each indicated at 72, and seven smaller gears, each indicated at 74, respectively mounted on seven rotatably mounted shafts, each indicated at 76. As shown, the large spur gear 68 of the group of gears 66 engages the bottom, right-hand larger gear 72a of the gear train 56 for driving the rotation of all of the gears 72, 74 of the gear train 56. The arrangement is such that the gear train 56 includes at least one large gear (the top, left-hand gear) designated 72b which defines a slow speed gear that is rotatable at a relatively slow rate of speed, and at least one other large gear (the top, right-hand gear) designated 72c which defines a fast speed gear that is rotatable at a relatively fast rate of speed. These two gears 72b, 72c are engagable with the rack member 58 as illustrated in FIG. 3 and FIG. 6, respectively.

Figure 7:
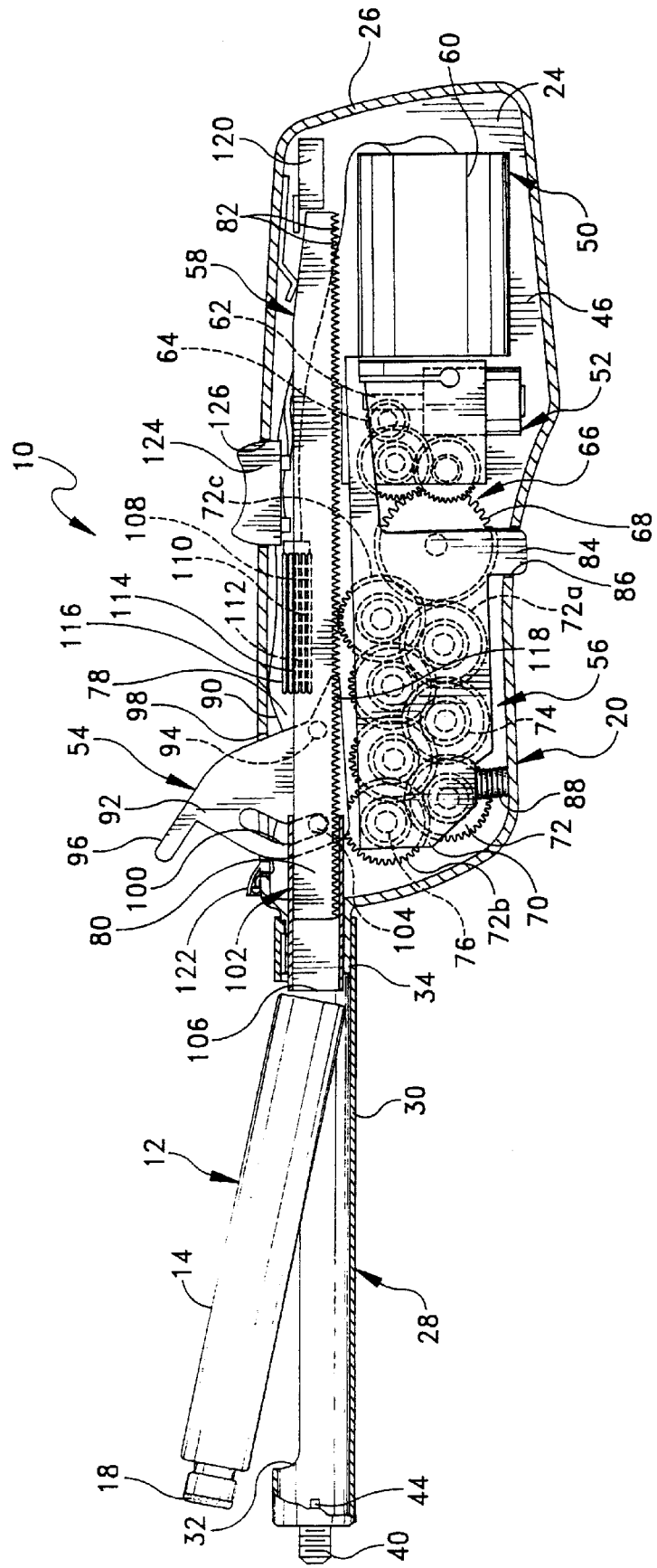
FIG. 7 is a cross-sectional view similar to FIGS. 3 through 6 illustrating the apparatus in fast reverse operating mode.

More specifically, the rack member 58, which is axially slidable within a channel (not shown) formed on the interior surfaces of the housing 20, comprises an elongate body 78 having an end portion 80 which is engagable with the piston 16 of the carpule 12 and teeth 82 formed on a side of the body 78 which are selectively engagable with one of the slow and fast speed gears. FIGS. 3 and 7 illustrate the rack member 58 in a retracted position in which it is completely positioned within the chamber 46 of the housing 20 and the end portion 80 of the rack member 58 is spaced from the carpule piston 16. FIGS. 4 through 6 illustrate the rack member 58 in an extended position in which one of the slow and fast speed gears 72b, 72c engages the teeth 82 of the rack member 58 for moving it linearly along axis A to a position in which the end portion 80 engages the carpule piston 16. The rack member 58 moves linearly along axis A towards the carpule 12 for causing the dispensing of fluid from the carpule 12 and through the needle 42 at a slow and controlled rate.

The frame 70 is pivotally mounted within the chamber 46 of the housing 20 so as to effect the selective engagement of either the slow speed gear 72b or the fast speed gear 72c with the teeth 82 of the rack member 58. The frame 70 has an outwardly protruding member 84 which is accessible from outside of the housing 20 through an opening 86 formed in the outer peripheral wall 26 of the housing 20 for moving the frame 70 between a first position in which the slow speed gear 72b is engaging the teeth 82 of the rack member 58 and a second position in which the fast speed gear 72c is engaging the teeth 82. As shown, a spring 88, engagable at one of its ends with the frame 70 and at its other opposite end with the wall 26 of the housing 20, is further provided for biasing the frame 70 to its first position in which the slow speed gear 72b drives the rack member 58. By engaging the member 84 of the frame 70 and pivoting the frame 70 upwardly, the bias of spring 88 is overcome and the fast speed gear 72c engages or meshes with the teeth of the rack member 58. The fast speed gear 72c preferably rotates at approximately 16 RPM (thereby resulting in the rack member moving at 25 inches per minute). By virtue of the five intermediate pairs of gears 72, 74 disposed between the slow speed and fast speed gears 72b, 72c, the speed of the slow speed gear 72b is reduced to approximately 2 RPM (thereby resulting in the rack member moving at 3 inches per minute).

The switch 54 is suitably electrically connected with the battery 60 and the motor 52 by wires 90 in the well-known fashion for selectively operating the motor 52 from a non-operable condition in which the battery 60 is electrically disconnected from the motor 52 to an operable condition in which the battery 60 is electrically connected to the motor 52 and supplies power thereto. The switch 54 includes a depressible lever 92 pivotally mounted on the housing 20 by a protrusion 94 which is held captive by the housing 20 in such a manner that an engaging portion 96 of the lever 92 is accessible from outside the housing 20. The engaging portion 96 extends through an opening 98 formed in the outer peripheral wall 26 of the housing 20 and is capable of being pressed by the operator of the apparatus 10 by the operator's forefinger. Thus, the amount of force required to pivot the lever 92 downwardly into the chamber 46 of the housing 20 is relatively slight thereby enabling the apparatus 10 to be held like a pen and not like a gun.

The lever 92 further has a curved or arcuate portion having a slot 100 formed therein. The curved portion of the lever 92 is engagable with an axially slidable, annular sleeve generally indicated at 102 which is disposed around the rack member 58 between the curved portion of the lever 92 and the body 14 of the carpule 12. The arrangement is such that when the engaging portion 96 of the lever 92 is pressed downwardly as illustrated in FIG. 4, the curved portion engages the annular sleeve 102 for axially moving it slightly towards the carpule 12 thereby dispensing a small amount of fluid from the carpule.

More specifically, the annular sleeve 102 has a detent member 104 which is received in the slot 100 of the lever 92 and rides within the slot as the lever is pressed downwardly. As the lever 92 moves downwardly, the detent member 104 of the sleeve 102 moves axially towards the carpule 12 whereby the end 106 of the sleeve 102 engages the body 14 of the carpule 12. Conversely, as the lever 92 is spring biased upwardly, the detent member 104 is withdrawn back into the housing 20 thereby moving the sleeve 102 axially away from the carpule 12. Thus, as illustrated in FIG. 4, when the curved portion of the lever 92 engages the detent member 104 of the sleeve 102 in response to a person applying a downward force on the engaging portion 96 of the lever 92, the end 106 of the sleeve 102 slides axially along axis A so as to cause the slight movement of the body 14 (e.g., approximately 1.5 mm) thereby compressing the resilient gasket 18 and dispensing a small amount of fluid from the carpule 12 through the needle 42. If the needle 42 is slightly penetrating the tissue of the patient requiring anesthetizing, by releasing the lever 92, a small amount of fluid is drawn back through the needle 42 and into the carpule 12. By releasing the lever 92, the camming action of the detent member 104 within the slot 100 causes the rearward movement of the sleeve 102. This aspirating step enables the operator of the apparatus 10 giving the injection to determine whether the needle 42 is penetrating a major blood vessel.

As mentioned briefly above, the apparatus' motor 52 can operate at one of three speeds, thus enabling the apparatus 10 to operate at six separate speeds, i.e., three "slow" speeds and three "fast" speeds, depending upon whether the slow or fast speed gear 72b, 72c is engaging the rack member 58. To change the speed of the motor 52, the lever 92 is either slightly pivoted, moderately pivoted or nearly fully pivoted (see FIG. 5 which illustrates the nearly fully pivoted position), for respectively selecting a slow, intermediate and fast motor speed. The switch 54 further comprises three sets of thin, elongate contacts which are in electrical communication with the battery 60 and the motor 52, and are operable for activating the motor 52 in one of its three respective speeds. As shown, there are five contacts, contacts 108, 110 constituting a first set of contacts, contacts 110, 112 constituting a second set of contacts, and contacts 112, 114 constituting a third set of contacts. The fifth contact 116 is a spare which is provided with the sets of contacts. The lever has a tail portion 118 which is engagable with the contacts 108, 110, 112, 114 and 116 when the engaging portion 96 is pressed downwardly by the person operating the apparatus 10. Thus, by moving the lever 92 to its slightly pivoted position, the first set of contacts 108, 110 are engaged by the tail portion 118 for operating the motor 52 at a first, relatively slow speed. Similarly, by moving the lever 92 to its moderately and nearly fully pivoted positions with the tail portion 118 (see FIGS. 5 and 6 for the nearly fully pivoted position), the second set of contact 110, 112 and third set of contacts 112, 114 are engaged for operating the motor 52 at a second (intermediate) speed and a third (fast) speed, respectively.

A limit switch 120, mounted within the chamber 46 of the housing 20 at its rearward end, is provided for cutting off the motor 52 upon being engaged by the other end of the rack member 58. This occurs when the rack member 58 is in its fully retracted position.

A further feature of the present invention is the provision of a pen light 122 mounted on the forward end of the housing 20 for illuminating the space in front of the dispensing apparatus 10 (i.e., the patient's mouth). The pen light 122 can be turned on and off by any suitable means, such as by a switch (not shown), and draws its energy from the battery 60. The electrical hook-up of the pen light 122 with the battery 60 can be accomplished in any conventional, well-known fashion.

In order to return the rack member 58 to its retracted position, a reversing switch 124, which is in electrical communication with the motor 52, is further provided. The reversing switch 124 extends through an opening 126 formed in the outer peripheral wall 26 of the housing 20 right behind the lever 92. The reversing switch 124 simply reverses the rotation of the shaft 62 of the motor, thereby reversing the rotation of the gears 72, 74 of the gear train 56. The reversing switch 124 enables the operator of the apparatus 10 to control the speed of the retraction of the rack member 58 in any one of six speeds; however, it has been found that best results are obtained by engaging the fast speed gear 72c with the teeth 82 of the rack member 58 and by pressing the lever 92 so that the third set of contacts 112, 114 are in engagement thereby retracting the rack member 58 into the housing 20 as quickly as possible.

Figure 8:
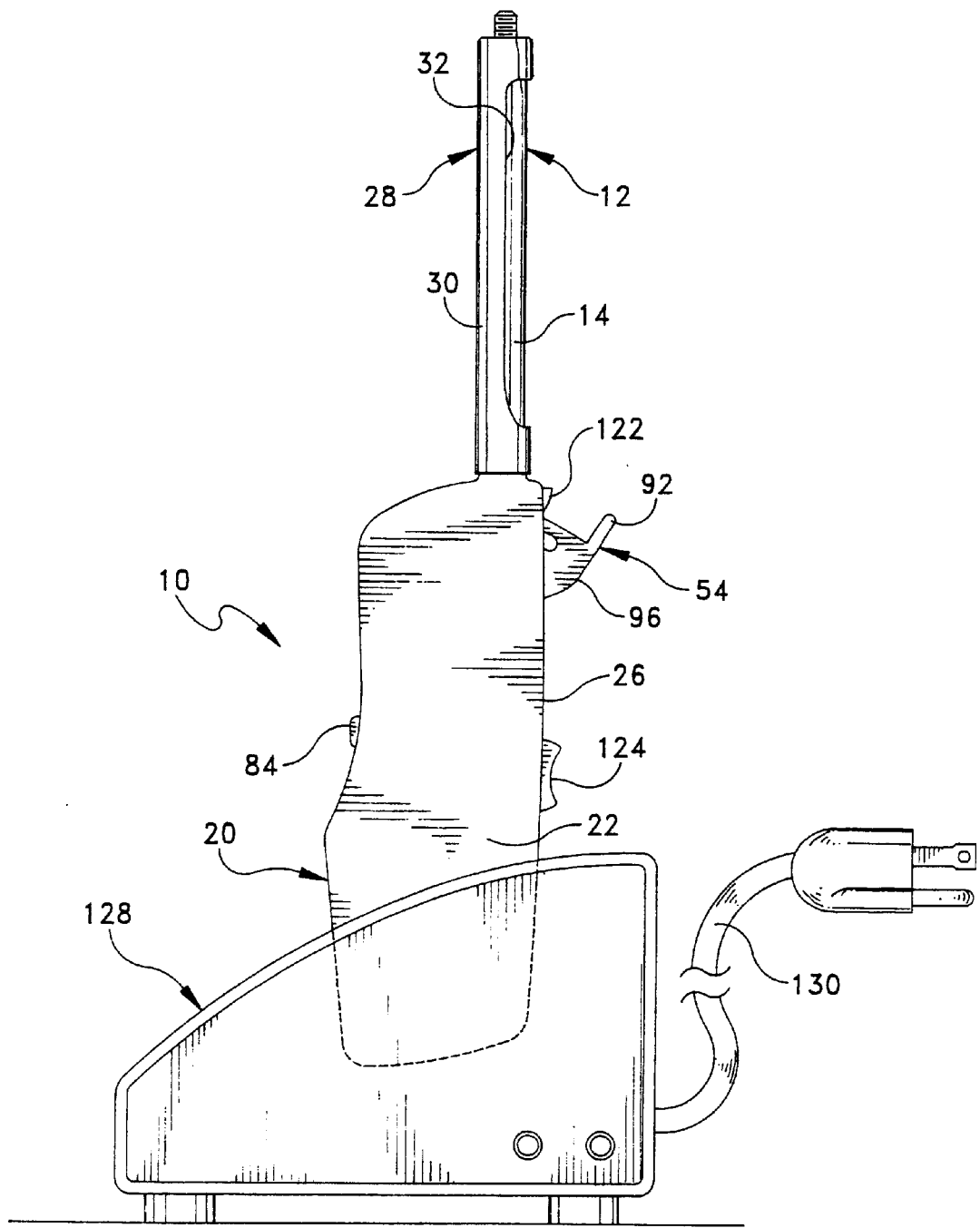
FIG. 8 is an elevational view of the apparatus seated in a battery recharging device.

Referring now to FIG. 8, there is illustrated the apparatus 10 of the present invention seated within a battery charging device, generally indicated at 128, for recharging the battery 60. The device 128 is preferably fabricated from any rigid material (e.g., plastic) and includes a plug 130 which plugs into a standard electrical wall outlet. Although not illustrated, the housing 20 of the apparatus 10 may be provided with a plug or receptacle which is in electrical communication with the battery 60 for supplying energy to the battery 60 when it is seated in the device 128. Such a system is well-known in the art of battery operated tools which require having their batteries recharged. A manifold design can be used to recharge multiple batteries at once and the apparatus can have lights indicated the need for battery recharging as is well-known in other apparatuses.

During use, the apparatus 10, having a charged battery 60, is assembled for use by mounting the carpule receiving member 28 onto the forward end of the housing 20. At this time, a needle 42 can be screwed onto the threaded portion 40 of the receiving member 28. Both of these component parts are removable from the housing 20 and from each other for sterilization purposes, or to be exchanged between patient use for a sterilized replacement member 28. Next, a carpule 12 is inserted through the slot 32 of the receiving member 28 in a position where it rests inside the receiving member 28 (see FIGS. 3 through 6). When inserting the carpule 12 into the receiving member 28, it is important to note that the rack member 58 is in its retracted position.

The rack member 58 is then moved linearly towards the piston 16 of the carpule 12 in either the slow or fast speed mode, depending upon the distance between the end portion 80 of the rack member 58 and the piston 16 of the carpule 12. Once the end portion 80 is in engagement with the piston 16 of the carpule 12, the lever 92 is slightly pivoted so as to engage the curved portion of the lever 92 with the detent member 104 of the sleeve 102, thereby moving the sleeve 102 linearly towards the carpule 12 for dispensing a small amount of fluid. Aspiration can be achieved by releasing the lever 92 thereby drawing fluid back into the carpule 12. The provision of this mechanical aspiration feature of the present invention makes it especially easy to perform the aspiration function.

To inject the fluid into the tissue penetrated by the needle 42, the lever 92 is pressed downwardly so as to engage the first set of contacts 108, 110 thereby energizing the motor 52. Preferably, the frame 70 of the gear train 56 is in its normally biased position wherein the slow speed gear 106 engages the teeth 82 of the rack member 58. The person operating the apparatus 10 can quicken the amount of fluid being dispensed into the tissue area by further pressing the lever 92 downwardly thereby engaging the second set of contacts 110, 112 or the third sets of contacts 112, 114. Since the slow speed gear 72b is driving the rack member 58, the speed of the movement of the rack member 58 is not extremely fast. It should be noted that by providing a completely mechanical actuating system, wherein pneumatic or hydraulic actuators are not involved, slow and uniform delivery of fluid is ensured.

Once the injection is given, and the needle 42 is removed from the tissue area of the patient's mouth, the rack member 58 is withdrawn into the chamber 46 of the housing 20 by pressing the reversing switch 124, moving the frame 70 of the gear train 56 to its fast mode by applying a force on the outwardly protruding member 84 of the frame 70, and pressing the lever downwardly so as to engage the third set of contacts 112, 114. By following these steps, the rack member 58 is quickly withdrawn into the chamber 46 of the housing 20. Upon engaging the limit switch 120, power to the motor 52 is cutoff and the rack member 58 is in its fully retracted position.

At this point, the carpule 12 is removed from the receiving member 28 in the manner illustrated in FIG. 7 and the carpule receiving member can be removed from the housing 20 for sterilization. When finished, the apparatus 10 is placed back in the battery recharging device 128 for recharging the battery 60.

As discussed above, pain is caused when an anesthetic is injected into the tissues at a rate which is too fast for the tissue to absorb the injected fluid. When this occurs, pressure within the tissue increases, causing the tissue at the injection site to stretch and become distended to accommodate the injected fluid volume. When the pressure within the tissue reaches a level such that the tissue reaches a maximum expandability level and the specific tissue's rate of absorbtion is exceeded, the brain is signaled to induce a painful response. The amount of pressure that each tissue can tolerate before experiencing pain varies depending on the distensibility and absorbtion rate of the tissue. For example, tissue which is more pliable will allow fluid to flow more freely through it, but is more susceptible to stretching and therefore will reach its maximum expandability level and induce a painful response at lower pressures than less pliable, firmly affixed tissue, which is capable of tolerating much higher injection pressures.

Figure 9:
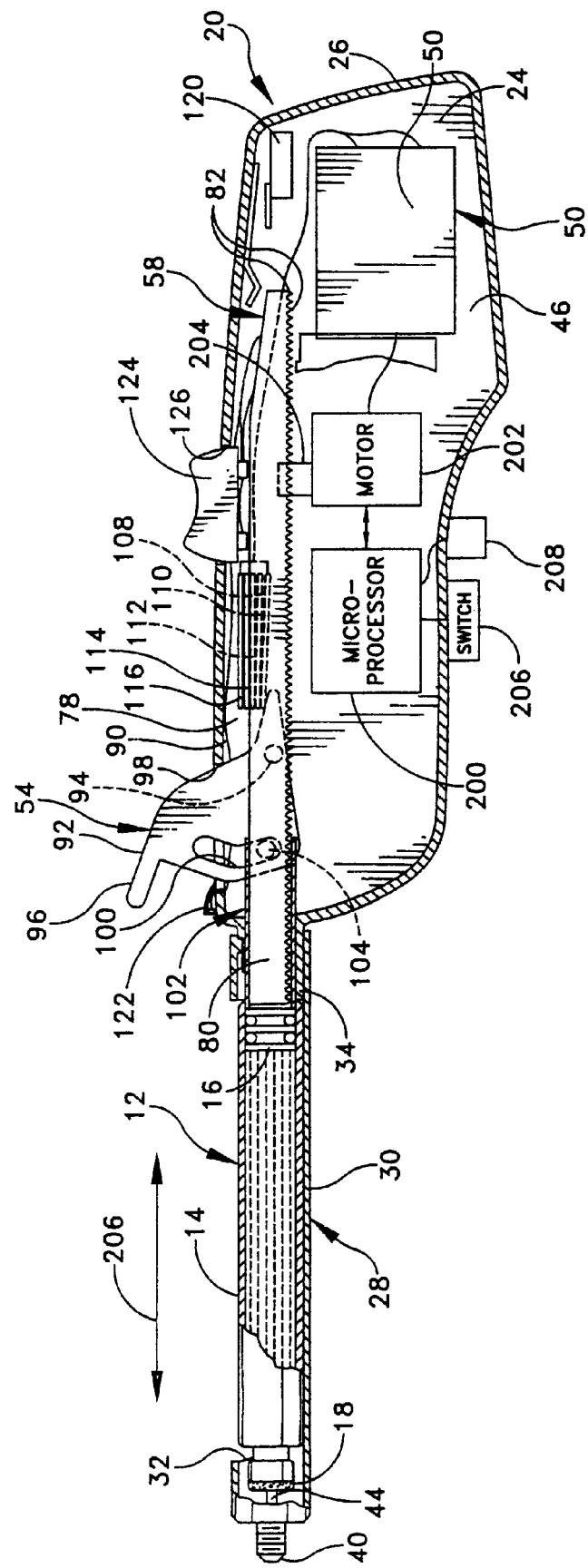
FIG. 9 is cross-sectional view illustrating a second embodiment of the apparatus of the present invention.

Referring now to FIG. 9, a second embodiment 10a of the fluid dispensing apparatus of the invention will be described.

In the embodiment shown in FIG. 9, corresponding reference numerals are used to indicate components which are identical to those shown in FIGS. 1–7. Each of the components which are common to apparatus 10 of FIGS. 1–7 and apparatus 10a of FIG. 9 operate in a similar manner as described with reference to FIGS. 1–7.

This embodiment differs from that shown in FIGS. 1–7 in the mechanism mounted within housing 20 for delivering the fluid from the carpule 12 through the needle 42. This mechanism, generally indicated in block form within housing 20 in FIG. 9, will now be described. As shown in FIG. 9, the apparatus 10a includes a microprocessor 200 and a reversible, variable speed motor 202. Microprocessor 200 and motor 202 replace motor 52 and gear train 56 of the embodiment of FIGS. 1–7. Motor 202 is connected to receive power from power supply 50 over line 220 and is also connected to receive operating instructions from microprocessor 200 over line 222. Motor 202 is coupled to drive mechanism 204 which drives rack member 58 bidirectionally along axis 206. When driven in one direction, drive mechanism 202 to pushes piston 16 into carpule 12 to drive the anesthetic from carpule 12 through needle 42, when rack member 58 is driven in one direction by drive mechanism 204. When driven in a reverse direction, rack member 58 pulls piston 16 from carpule 12. Drive mechanism 204 may be constructed from any type of mechanism known in the art which is capable of driving rack member 58, such as a simple gear having teeth which mesh with teeth 82 of rack member 58. Motor 202 is capable of driving drive mechanism 204 at a wide variety of speeds in order to cause rack member 58 and, consequently, piston 16, to drive the anesthetic from carpule 12 into the patient's mouth at certain predetermined pressures. As is described in greater detail below, microprocessor 200 is programmed to selectably drive motor 202 at a number of different predetermined speeds which correspond to the different pressures at which the anesthetic is injected into the patient's mouth.

As described above, different injection sites within the mouth and body require different injection pressures. Maximum injection pressures can range from between 17,061 mmHg to 34,122 mmHg. Injection sites that are least distensible have the highest maximum injection pressures, while more distensible sites require lower injection pressures. For example, the interosseous region of the mouth can tolerate injections up to a pressure of 29,559 mmHg, the incisive papilla region can tolerate injections up to a pressure of 20,680 mmHg, the periodontal ligament can tolerate injections up to a pressure of 17,630 mmHg, the hard palate can tolerate injections up to a pressure of 11,322 mmHg, the intrapulpol region can tolerate injections up to a pressure of 8,918 mmHg and the inferior alveolar region can tolerate injections up to a pressure of 450 mmHg. These figures are determined using an injection device outfitted with a pressure transducer to determine an average pressure for each potential injection site. The average pressure is determined by obtaining pressure readings from a test group of patients for each potential injection site.

Apparatus 10a includes an adjustment mechanism 206 which provides to microprocessor 200, over line 224, the pressure at which the anesthetic is to be driven into the injection site within the patient's mouth. Microprocessor 200 is programmed to drive motor 202 at predetermined speeds which correspond to the injection pressures required for the different injection sites. Adjustment mechanism 206 allows the operator of the apparatus to select the pressure at which the anesthetic is to be injected into the patient. Accordingly, adjustment mechanism 206 allows the operator to select from a number of settings, each setting corresponding to an injection pressure which is programmed into microprocessor 200. Preferably, adjustment mechanism 206 is a dial which can be rotated to select different pressures, although it will be obvious to those skilled in the art that a number of different types of adjustment mechanisms may be used to select an injection pressure. A start/stop button 208, which is coupled to power supply 50 over line 228 is depressed or released to instruct microprocessor 200 to respectively begin or end the delivery of anesthetic. A display unit 212, which is built into housing 20, receives the selected pressure from microprocessor 200 and displays the pressure to assist the operator in setting the desired pressure. Preferably, display unit 212 provides a digital readout of the selected pressure.

During use of apparatus 10a, the operator selects an injection pressure using adjustment mechanism 206. The operator then penetrates the injection site 1 to 2 mm and depresses button 208 to begin the flow of anesthetic into the injection site. At first, the anesthetic flows slowly in order to overcome the breakaway force of the piston 16. After 1 to 2 seconds, the microprocessor 200 instructs the motor 202 to drive mechanism 204 at a speed which corresponds to the desired injection pressure. When the injection is complete, the button 208 is released and microprocessor 200 instructs motor 202 to reverse direction in order to aspirate the injection site. This process may be repeated until the desired amount of anesthetic is delivered to the injection site.

Microprocessor 200 monitors the position of piston 16 by counting the number of revolutions turned by motor 202. At a predetermined number of rotations, the microprocessor calculates the amount of anesthetic remaining in the carpule 12. When the microprocessor 200 determines that the carpule 12 is empty, the microprocessor instructs the motor 202 to reverse completely to allow a full carpule to be inserted into carpule receiving member 28.

A third embodiment 10b of the present invention will now be described with reference to FIG. 10. In the embodiment shown in FIG. 10, corresponding reference numerals are used to indicate components which are identical to those shown in FIG. 9. Each of the components which are common to apparatus 10a of FIG. 9 and apparatus 10b of FIG. 10 operate in a similar manner as described with reference to FIG. 9.

Figure 10:
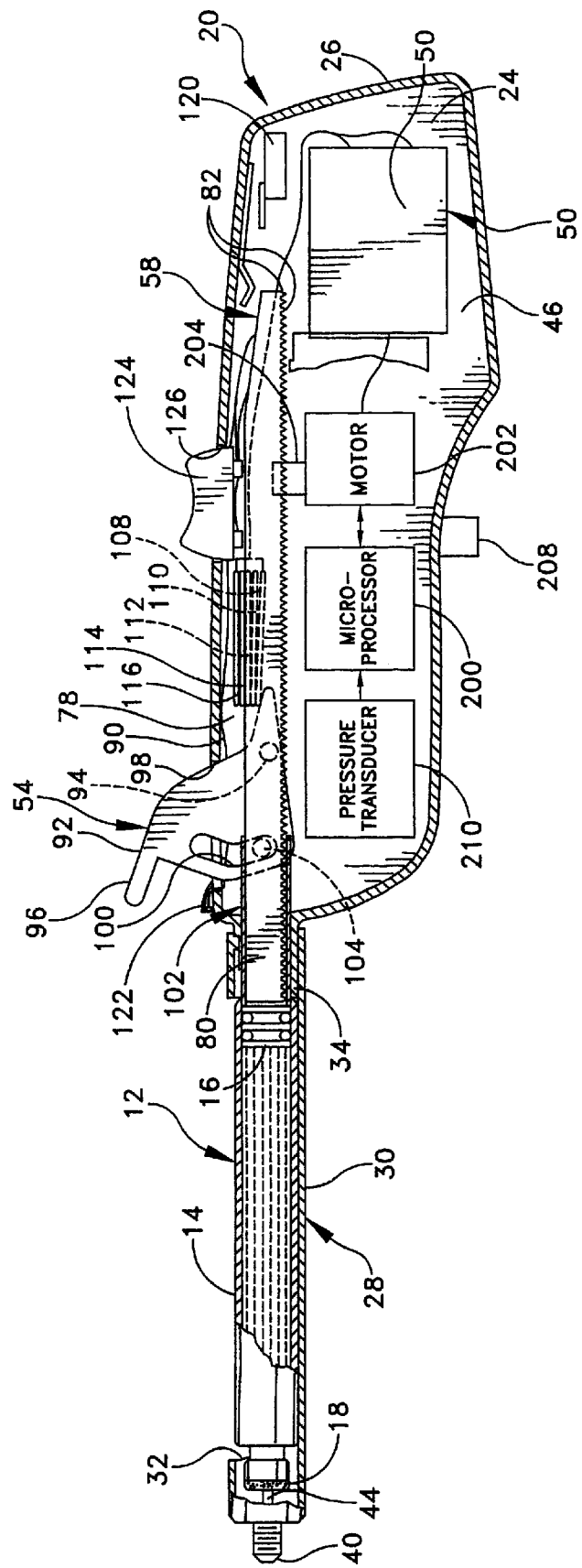
FIG. 10 is cross-sectional view illustrating a third embodiment of the apparatus of the present invention.

While in the embodiment of FIG. 9, the injection pressures are predetermined and preprogrammed into microprocessor 200, the embodiment of FIG. 10 allows the injection pressures to be determined at the time of the injection. This allows the operator to deliver the anesthetic at a pressure which corresponds specifically to the particular patient who is receiving the anesthetic. This is done by including a pressure transducer 210 within housing 20 of apparatus 10b, which is coupled to microprocessor 200 via line 232.

In use, a needle attached to the apparatus 10b as described above, is inserted into the injection site, and a small amount of anesthetic is delivered to the site by depressing button 208. After 1 to 2 seconds, the flow of anesthetic is stopped and the pressure transducer 210 measures the natural pressure of the tissue at the injection site. Such a measurement taken at zero fluid flow represents a pressure close to or slightly above the tissue's natural pressure. The pressure transducer 210 sends this measurement to the microprocessor 200 over line 232, which then instructs motor 202 to operate at a speed which will allow drive mechanism 204, rack member 58 and piston 16 to deliver anesthetic to the injection site at a pressure which is slightly less than the tissue's natural pressure. This prevents delivery of the anesthetic at a speed which will cause the tissue pressure to increase and over-distend, resulting in pain. For example, microprocessor 200 may instruct motor 202 to operate at a speed which results in an injection pressure which is 95 percent of the pressure measured by the pressure transducer 210. This ensures that the tissue's natural pressure, as measured by the pressure transducer, is not exceeded. By monitoring the injection pressure, pain which would take place if the pressure exceeded the tissue's natural pressure can be avoided.

The injection pressure, as determined by the microprocessor, is displayed by display 212. This allows the operator to record the injection pressure for the patient's records. A port 242 is provided to enable the injection pressure, which may be stored in a memory of microprocessor 200, to be downloaded into a computer for future reference, should an injection at the same site be required at a later time.

In this embodiment, an override device 240 is also provided, which enables the operator to override the 95% injection pressure calculated by the microprocessor 200 in order to lower the injection pressure below the 95% figure. For instance, if at 95% of the tissue's measured pressure, the patient is still experiencing discomfort, the operator can utilize the override device 240 to decrease the injection pressure. Preferably, override device 240 is in the form of a dial, which when rotated, instructs the microprocessor 200 to increase or decrease the injection pressure or speed. The injection pressure is monitored by the operator through display unit 212.

The microprocessor 200 is also programmed to recognize if the pressure reading measured by the pressure transducer 210 is much different than the injection pressure set in the microprocessor. For example, if the pressure measured by the pressure transducer 210 is less than 80% or more than 105% of the injection pressure set in the microprocessor, the microprocessor instructs the motor 202 to stop the forward injection and to reverse in order to move piston 16 in a reverse direction to aspirate the injection site In this aspiration mode, the operator is able to determine whether a blood vessel has been entered by the needle 42. If this is the case, in the aspiration mode, a stream of blood would appear in the carpule, signifying that a blood vessel has been entered. The operator would then redirect the needle to avoid the blood vessel. When the pressure transducer 210 measures a tissue pressure which corresponds to the injection pressure set in the microprocessor 200, the microprocessor 200 resumes the forward injection process by instructing the motor 202 to operate to cause the rack member 58 to drive piston 16 forward. A control 260, preferably in the form of a button, is provided to allow the operator to initiate the above-described aspiration mode manually.

The present invention is an automated fluid delivery apparatus which can employ several motor technologies, including direct current motors, stepper motors and piezoelectric motors. The advantage of the construction of the present invention is that the apparatus delivers fluid in a microprocessor-controlled, uniform, and smooth manner which is free of surge that is present with manual injection devices. Hand or manual syringes emit fluids less slowly, less smoothly, and sporadically. The invention releases fluids at a slower, more uniform rate and the fluid, instead of balling up (tending to gather in a mass) as is the case with hand syringes. The application of fluid in a controlled manner enables the fluid to be gradually absorbed by the tissues and nerves. This makes the present invention more effective since there is less pressure exerted on the tissues and nerves, and the fluid does not dissect or force its way into them. Thus, the invention substantially eliminates the pain caused by the surging of fluid associated with manual injections.

Furthermore, there is an improved safety factor due to the slow, uniform flow of fluid. Not only does the application of fluid with the invention minimize pain, but it also acts to prevent shocking the patient's vascular and nervous systems. The invention allows for aspiration so the clinician applying the fluid can determine whether the needle is penetrating a blood vessel. And even if the needle has entered the blood vessel, the fluid is administered so slowly by the invention that vagal/vagal type of reactions are avoided. Moreover, the precise injection pressures can be recorded by the operator for use in future procedures with each patient.

Needle puncture pain is lessened owing to the technique of allowing the anesthetic to flow slowly and continuously ahead of the penetrating needle. This application diminishes pain that could occur from the fast needle penetrating associated with manual needles. Also, reloading with second, third, etc., carpules of anesthetic (or medication) is readily accomplished due to the quick withdrawal feature of the apparatus which enables the rack member 58 to be withdrawn within the housing 20.

While there is shown and described herein certain specific structure embodying the invention, it will be manifest to those skilled in the art that various modifications and rearrangements of the parts may be made without departing from the spirit and scope of the underlying inventive concept. For example, other driving devices, such as hydraulic devices, may be used to drive the drive mechanism. and that the same is not limited to the particular forms herein shown and described except insofar as indicated by the scope of the appended claims.

What is claimed is:

1. A method for injecting fluid into oral tissue comprising the steps of:

determining a tissue injection pressure for an injection site of said oral tissue; and injecting said fluid into said injection site at a pressure which is not greater than said tissue injection pressure.

2. The method of claim 1, wherein said determining step injecting step are performed substantially concurrently.

3. The method of claim 1, wherein said determining step is performed before said injecting step.

4. The method of claim 1, wherein said fluid is an anesthetic.

5. The method of claim 2, wherein said injecting step comprises delivering said fluid into said oral tissue with a needle and said determining step comprises measuring said tissue injection pressure with a pressure transducer mounted proximate a tip of said needle.

6. A fluid dispensing apparatus for dispensing fluid from a carpule having an axially slidable piston, said apparatus comprising:

a hollow housing having an elongate chamber formed therein, said housing extending generally along an axis and being constructed and arranged to be gripped within a person's hand;

a carpule receiving member which is attached to said housing at one end thereof, said carpule receiving member having means for receiving a needle at its other opposite end and being adapted to receive a carpule having fluid therein which is ejected through the needle;

a power supply located within the chamber of the housing;

a motor energized by said power supply, said motor being located within the chamber of the housing and having a drive mechanism which is rotatably driven;

a switch accessible from outside the housing and being in electrical communication with said power supply and motor for selectively operating said motor from a non-operable condition in which the power supply is electrically disconnected from the motor to an operable condition in which the power supply is electrically connected to the motor and supplies power thereto;

a microprocessor for controlling an operating speed of said motor;

a rack member disposed within the chamber of the housing along said axis, said rack member comprising an elongate body having an end portion engagable with said piston of the carpule and teeth formed on a side thereof which are engagable with said drive mechanism for moving the rack member linearly from a position in which the end portion is spaced from the carpule piston to a position in which the end portion engages the carpule piston so as to effect the dispensing of fluid from the carpule and through the needle at a controlled rate;

wherein said microprocessor, by controlling said operating speed of said motor, controls a pressure at which said fluid is dispensed from said carpule.

7. A fluid dispensing apparatus for dispensing fluid from a carpule having a slidable piston, the apparatus comprising:

a motor coupled to said piston for bidirectionally driving said piston along a longitudinal axis of said carpule;

a microprocessor for controlling said motor, said microprocessor controlling a speed at which said motor drives said piston;

a power supply for supplying power to said motor and said microprocessor;

wherein said microprocessor is capable of driving said motor at a number of speeds, each of said number of speeds corresponding to a specific pressure at which said fluid is dispensed from said carpule; and wherein said microprocessor monitors an amount of fluid in said carpule by measuring a physical parameter of said motor.

8. The apparatus of claim 7, further comprising an adjustment mechanism for selecting one of said number of speeds.

9. The apparatus of claim 7, wherein said physical parameter is a number of turns made by said motor while driving said piston.

10. A method for injecting fluid in to tissue comprising the steps of:

determining a tissue injection pressure for an injection site of said tissue;

injecting said fluid into said injection site at a pressure which is not greater than said tissue injection pressure;

said determining step and said injecting step being performed substantially concurrently;

said injecting step comprising the delivering of said fluid into said tissue with a needle;

said determining step comprising the measuring of said tissue injection pressure with a pressure transducer mounted proximate the tip of said needle;

said injecting step further comprising the inserting of said needle tip into said injection site to deliver an amount of said fluid into said injection site;

momentarily ceasing said delivery of fluid to said injection site while said determining step is being performed; and resuming said delivery of fluid at said tissue injection pressure determined during said determining steps.

11. A fluid dispensing apparatus for dispensing fluid from a carpule having a slidable piston, the apparatus comprising:

a motor coupled to said piston for bidirectionally driving said piston along a longitudinal axis of said carpule;

a microprocessor for controlling said motor, said microprocessor controlling a speed at which said motor drives said piston;

a power supply for supplying power to said motor and said microprocessor;

wherein said microprocessor is capable of driving said motor at a number of speeds, each of said number of speeds corresponding to a specific pressure at which said fluid is dispensed from said carpule; and wherein said carpule includes a needle for inserting into tissue for injecting said fluid into an injection site of the tissue, said microprocessor being programmed with said number of speeds to instruct said motor to inject said fluid into said tissue at a corresponding pressure, said apparatus further comprising a pressure-measuring device for continuously obtaining a measurement of a pressure of said tissue at said injection site.

12. The apparatus of claim 11, wherein said microprocessor receives said measured pressure and instructs said motor to operate at a speed which corresponds to an injection of said fluid at an injection pressure proximate said measured pressure.

13. The apparatus of claim 12, wherein said pressure-measuring device comprises a pressure transducer mounted proximate said needle, said apparatus further comprising an override mechanism which reduces said injection pressure by a predetermined amount.

14. The apparatus of claim 12, further comprising a display device for displaying said injection pressure.

15. The apparatus of claim 12, wherein said microprocessor stores said measured pressure and said injection pressure in a memory of said microprocessor, said apparatus further comprising a data output port for allowing said stored measurement and injection pressures to be downloaded to an external device.

16. The apparatus of claim 12, further comprising an aspiration mechanism for initiating an aspiration operation of said apparatus when said measured pressure is determined by said microprocessor to be significantly different from said injection pressure.

17. The apparatus of claim 11, wherein said microprocessor receives said measured pressure and instructs said motor to operate at a speed which corresponds to an injection of said fluid at an injection pressure below said measured pressure.

* * * * *